(12) United States Patent
Zhang et al.

(10) Patent No.: US 11,591,292 B2
(45) Date of Patent: Feb. 28, 2023

(54) PREPARATION OF CATIONIC SURFACTANTS

(71) Applicant: Saudi Arabian Oil Company, Dhahran (SA)

(72) Inventors: Xuan Zhang, Beijing (CN); Ming Han, Dhahran (SA); Jinxun Wang, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 17/551,945

(22) Filed: Dec. 15, 2021

(65) Prior Publication Data

US 2022/0106261 A1    Apr. 7, 2022

Related U.S. Application Data

(62) Division of application No. 16/942,565, filed on Jul. 29, 2020, now Pat. No. 11,286,232.

(51) Int. Cl.
*C07C 237/52* (2006.01)
*C07C 231/02* (2006.01)
(Continued)

(52) U.S. Cl.
CPC .......... *C07C 237/52* (2013.01); *C07C 231/02* (2013.01); *C07C 233/36* (2013.01); *C07C 233/38* (2013.01); *C09K 8/584* (2013.01)

(58) Field of Classification Search
None
See application file for complete search history.

(56) References Cited

U.S. PATENT DOCUMENTS 4,274,283 A    6/1981  Maus et al.
4,283,321 A    8/1981  Chakrabarti et al.
(Continued)

FOREIGN PATENT DOCUMENTS

CA       2384108      7/2011
CN     103806905      5/2014
(Continued)

OTHER PUBLICATIONS

PCT International Search Report and Written Opinion in International Appln. No. PCT/US2021/043630, dated Nov. 22, 2021, 14 pages.

(Continued)

*Primary Examiner* — Sudhakar Katakam
*Assistant Examiner* — Jennifer C Sawyer
(74) *Attorney, Agent, or Firm* — Fish & Richardson P.C.

(57) ABSTRACT

Compositions that include cationic surfactants and methods of synthesizing compositions that include cationic surfactants. The surfactants include a quaternary amine and a saturated or unsaturated alkyl chain with 4 to 28 carbons. The surfactants can be generated by reacting a fatty acid modified with an amino alkyl group and an epihalohydrin in the presence of a base. The cationic surfactants can be generated by reacting a fatty acid modified with an amino alkyl group, an epihalohydrin, and a carboxylic acid. The cationic surfactants can be generated by reacting a carboxylic acid, an epihalohydrin, and a catalyst to afford a halo-substituted alkyl ester, followed by reacting the halo-substituted alky ester with a fatty acid modified with an amino alkyl group.

5 Claims, 14 Drawing Sheets

(51) Int. Cl.
C07C 233/36 (2006.01)
C07C 233/38 (2006.01)
C09K 8/584 (2006.01)

(56) References Cited

U.S. PATENT DOCUMENTS

| | | |
|---|---|---|
| 4,526,947 A | 7/1985 | Castner |
| 4,691,558 A | 9/1987 | Vinson et al. |
| 4,719,423 A | 1/1988 | Vinegar et al. |
| 4,979,390 A | 12/1990 | Schupack et al. |
| 5,101,903 A | 4/1992 | Llave et al. |
| 5,387,865 A | 2/1995 | Jerosch-Herold et al. |
| 6,414,170 B1 | 7/2002 | Kim et al. |
| 7,169,745 B2 | 1/2007 | Kasturi et al. |
| 7,254,091 B1 | 8/2007 | Gunning |
| 8,260,589 B1 | 9/2012 | Kumar |
| 9,388,263 B2 | 7/2016 | Nakano et al. |
| 2009/0259446 A1 | 10/2009 | Zhang |
| 2010/0234252 A1 | 9/2010 | Moradi-Araghi et al. |
| 2011/0004447 A1 | 1/2011 | Hurley et al. |
| 2012/0221306 A1 | 8/2012 | Hurley et al. |
| 2012/0273193 A1 | 11/2012 | Sen et al. |
| 2012/0281883 A1 | 11/2012 | Hurley et al. |
| 2013/0180327 A1 | 7/2013 | Frederick |
| 2013/0235412 A1 | 9/2013 | Baldwin |
| 2014/0076544 A1 | 3/2014 | Lecerf et al. |
| 2014/0144628 A1 | 5/2014 | Moradi-Araghi et al. |
| 2016/0305922 A1 | 10/2016 | Narang et al. |
| 2017/0285122 A1 | 10/2017 | Kaditz et al. |
| 2022/0073662 A1 | 3/2022 | Zhang et al. |

FOREIGN PATENT DOCUMENTS

| | | |
|---|---|---|
| CN | 108642879 | 10/2018 |
| EP | 0474284 | 3/1992 |
| GB | 2262117 | 6/1993 |
| WO | WO 2010105070 | 9/2010 |
| WO | WO 2012061098 | 5/2012 |
| WO | WO 2014003596 | 1/2014 |
| WO | WO 2014082001 | 5/2014 |
| WO | WO 2019231479 | 12/2019 |

OTHER PUBLICATIONS

PCT International Search Report and Written Opinion in International Appln. No. PCT/US2021/049670, dated Dec. 13, 2021, 15 pages.
Al-Muntasheri et al., "Gelation Kinetics and Performance Evaluation of an Organically Crosslinked Gel at High Temperature and Pressure," SPE Journal, Sep. 2008, 337-345, 8 pages.
Al-Muntasheri et al., "Viscoelastic properties of a high temperature cross-linked water shut-off polymeric gel," Journal of Petroleum Science and Engineering, Apr. 2006, 55:2007 (56-66), 11 pages.
Alshehri et al., "Pore-Level Mechanics of Forced and Spontaneous Imbibition of Aqueous Surfactant Solutions in Fractured Porous Media," SPE 124946, Society of Petroleum Engineers (SPE), presented at the 2009 SPE Annual Technical Conference and Exhibition, Oct. 4-7, 2009, 17 pages.
Baskar et al., "Associated structures of aqueous solution of comb-like polymers from 2-acrylamido-2-methyl-1-propanesulfonic acid, dodecylmethacrylate and poly (ethyleneglycol) acrylate macromonomer," Polymer, 2004, 45: 6507-6517, 11 pages.
Bou-Mikael, "Design and Optimization of 2.5 Dimension Porous Media Micromodel for Nanosensor Flow Experiments," A Thesis Submitted to the Graduate Faculty of the Louisiana State University and Agricultural and Mechanical College in Partial Fulfillment of the Requirements for the Degree of Masters of Science in Chemical Engineering in the Gordon A. and Mary Cain Department of Chemical Engineering, May 2012, 84 pages.
Brown et al "Experimental observation of fluid flow channels in a single fracture," Journal of Geophysical Research, 103:B3 (5125-5132), Mar. 10, 1998, 8 pages.
Bryant et al., "Influence of Syneresis on Permeability Reduction by Polymer Gels," SPE35446, Society of Petroleum Engineers (SPE), SPE Production & Facilities, Nov. 1996, 7 pages.
Buchgraber et al., "The Displacement of Viscous Oil by Associative Polymer Solutions," SPE 122400, Society of Petroleum Engineers (SPE), presented at the 2009 SPE ATCE Annual Conference and Exhibition, Oct. 4-7, 2009, 19 pages.
Chang et al., "Effective Porosity, Producible Fluid and Permeability in Carbonate from Nmr Logging," SPWLA-1994-A, Society of Petrophysicists and Well-Log Analysts (SPWLA), presented at the SPWLA 35th Annual Logging Symposium, Jun. 19-22, 1994, 2 pages, Abstract only.
Chen et al., "Pore-Connectivity Based Permeability Model for Complex Carbonate Formations," Sociey of Petrophysicists and Well-Log Analysts (SPWLA), SPLWA 49th Annual Logging Symposium, May 25-28, 2008, 11 pages.
Chu et al., "A facile route towards the preparation of ultra-long-chain amidosulfobetaine surfactants," Synlett, 16: 2655-2658, 2009, 4 pages.
Chu et al., "Wormlike micelles and solution properties of a C22-tailed amidosulfobetaine surfactant," Langmuir, 26:11 (7783-7791), 2010, 9 pages.
Diacomo et al., "Mechanism of Polyacrylamide Gel Syneresis Determined by C-13 NMR," SPE 11787, Society of Petroleum Engineers (SPE), International Symposium on Oilfield and Geothermal Chemistry, Jun. 1-3, 1983, 8 pages.
Freedman et al., "Hydrcarbon Saturation and Viscosity Estimation From Nmr Logging in the Belridge Diatomite," SPWLA-1997-v38n2a1, Society of Petrophysicists and Well-Log Analysts (SPWLA), the Log Analyst, 38:2, Mar. 1997, 2 pages, Abstract only.
Haddad et al., "So What is the Reservoir Permeability?" SPE 63138, Society of Petroleum Engineers (SPE), presented at the Annual Technical Conference and Exhibition, Oct. 1-4, 2000, 24 pages.
Hajizadeh et al., "An Algorithm for 3D Pore Space Reconstruction from a 2D Image Using Sequential Simulation and Gradual Deformation with the Probability Perturbation Sampler," Transport in Porous Media, Kluwer Academic Publishers, Do., 94:3 (859-881), Jun. 20, 2012, 23 pages.
Haralick et al., "Computer Classification of Reservoir Sandstones," Sep. 11, 1972, 171-177, 7 pages.
Hasiuk, "Making Things Geological: 3-D Printing in the Geosciences," The Geological Society of America (GSA), Groundwork, GSA Today, 24:8 (28-29), Aug. 2014, 2 pages.
He et al., "Comparison of Gelatin Behavior and Morphology of Resocinol—Hexamethylenetetramine—HPAM Gel in Bulk and Porous Media," Transport Porous Media, 2015, 109:377-392, 16 pages.
Hornbrook, "Visualization of Foam/Oil Interactions in a New, High Resolution Sandston Replica Micromodel," a Report Submitted to the Department of Petroleum Engineering of Stanford University in Partial Fulfillment of the Requirements for the Degree of Master of Science, Sep. 1991, 48 pages.
Inwood, "High-Resolution, Microvisual Study of High Mobility Ratio, Immiscible Displacements," a Thesis Submitted to the Department of Petroleum Engineering of Stanford University in Partial Fulfillment of the Requirements for the Degree of Master Science, Jun. 2008, 104 pages.
Ishutov et al., "3-D Printing Artificial Reservoir Rocks to Test their Petrophysical Properties," Search and Discovery Article #41427, Aug. 29, 2014, 18 pages.
Jaber, "Low Tension Methods for Fractured Resources," a Thesis Submitted to the Department of Energy Resources Engineering of Stanford University in Partial Fulfillment of the Requirements for the Degree of Master of Science, Jun. 2009, 82 pages.
Kwak et al., "Close Monitoring of Gel Based Conformance Control by NMR Techniques," SPE-183719-MS-MS, Society of Petroleum Engineers (SPE), presented at the SPE middle East Oil and Gas Show and Conference, Mar. 6-9, 2017, 15 pages.
Li et al., "Synthesis, evaluation and aqueous solution behavior of the cationic fluorinated hydrophobically associating polyacrylamide," Journal of Polymer Research, 2019, 26:35, 11 pages.

(56) References Cited

OTHER PUBLICATIONS

Lu et al., "An advanced method for the preparation of erucyl dimethyl amidopropyl betaine and acid solution properties," Tenside Surfactants Detergents, 49:6 (TSI 10215-25.9.12 dk/stm köthen), 2012, 6 pages.

Maiti and De, "RAFT polymerization of fatty acid containing monomers," RSC Advances, RSC Publishing, 3: 24983, 2013, 9 pages.

Natarajan et al., "Control of In-Situ Gelation Time for HPAAM-Chromium Acetate Systems," SPE 39696, Society of Petroleum Engineers (SPE), presented at the 1998 SPE/DOE Improved Oil Recovery Symposium, Apr. 19-22, 1998, 13 pages.

Qi et al., "Synthesis, Characterization, and Solution Behavior of a Long-Chain Hydrophobic Association Anionic Acrylamide/2-Acrylamido-2-Methylpropanesulfonic Acid/n-Octyl Acrylate Terpolymers," Arabian Journal for Science and Engineering, 2017, 42:6 (2425-2432), 8 pages.

Rangel-German et al., "A Micromodel Investigation of Two-Phase Matrix-Fracture Transfer Mechanisms," Water Resources Research, 42:W03401, Mar. 7, 2006, 13 pages.

Renoux et al., "Aqueous solution properties of hydrophobically associating copolymers," Progress Colloid and Polymer Science, 1994, 97:213-217, 5 pages.

Romero-Zeron et al., "Characterization of Crosslinked Gel Kinetics and Gel Strength by Use of NMR," SPE 86548, Society of Petroleum Engineers (SPE), presented at the SPE International Symposium and Exhibition on Formation Damage Control, Feb. 18-20, 2004, 12 pages.

Smith, "Hot New Additive Manufacturing Materials" in Protype / Manufacture Nov. 1, 2011, retrieved from URL <http://www.digitaleng.news/de/hot-new-additive-manufacturing-materials>, 2011, 12 pages.

Straley et al., "Core analysis by low field NMR," SCA-9404, Society of Core Analysis (SCA), presented at the 1994 International Symposium, Sep. 12-14, 1994, 14 pages.

Sydansk, "Acrylamide-Polymer/Chromium(III)-Carboxylate Gels for Near Wellbore Matrix Treatments," Society of Petroleum Engineers (SPE), SPE Advanced Technology Series, Jan. 1990, 1:1 (146-152), 7 pages.

Tsang et al., "Flow Channeling in a Single Fracture as a Two-Dimensional Strongly Heterogeneous Permeable Medium," Water Resources Research, 25:9 (2076-2080), Sep. 1989, 5 pages.

Vasquez et al., "Laboratory Evaluation of High-Temperature Conformance Olymer Systems," SPE 80904, Society of Petroleum Engineers (SPE), presented at the SPE Production and Operations Symposium, Mar. 22-25, 2003, 11 pages.

Wang et al., "The N-allyl substituted effect on wormlike micelles and salt tolerance of a C 22-tailed cationic surfactant" Soft Matter 13.40, Jan. 2017, 7425-7432, 8 pages.

Wang et al., "The Study of Porous Media Reconstruction using a 2D Micro-CT Image and MPS," Computational Intelligence and Software Engineering, Dec. 11, 2009, 5 pages.

Wu and Batycky, "Evaluation of miscibility from slim tube tests," PETSOC-90-06-06, Petroleum Society of Canada, Enhanced Oil Recovery, Journal of Canadian Petroleum Technology, JCPT 90-06-06, 29:6, Nov.-Dec. 1990, 9 pages.

Yamamoto et al., "Associative Properties in Water of Copolymers of Sodium 2-(Acrylamido)-2-methylpropanesulfonate and Methacrylamides Substituted with Alkyl Groups of Varying Lengths," Macromolecules Nov. 1, 2000, 33: 7852-7861, 10 pages.

Yang et al., "Self-assembly properties of ultra-long-chain gemini surfactants bearing multiple amide groups with high performance in fracturing fluid application," Colloids and Surfaces A: Physicochemical and Engineering Aspects, 523:62, 2017, 32 pages.

Yao et al., "Petrophysical characterization of coals by low-field nuclear magnetic resonance (NMR)," Fuel 89:7 (1371-1380), Jul. 2010, 10 pages.

Yu et al., "Synthesis of Novel Zwitterionic Heterogemini Surfactants Derived from Fatty Acid and Investigation of Their Behavior at the Air-Water Interface," Letters in Organic Chemistry, Aug. 2015, 12(8): 590-597, 7 pages.

Zhang et al., "Novel hydrophobically associative polyacrylamide with tunable viscosity," Chinese Chemical Letters, Feb. 2009, 20:1361-1365, 5 pages.

Zhong et al., "Associative behavior in aqueous solutions for a salt-thickening tetra-polymer with allyl-capped macro-monomer," Polymer Science, Ser. A, 2014, 56:4 (422-433), 12 pages.

Zhuang et al., "Permeability Modification with Sulfomethylated Resorcinol-Formaldehyde Gel System," SPE 37245-MS, Society of Petroleum Engineers (SPE), presented at the 1997 SPE International Symposium on Oilfield Chemistry, Feb. 18-21, 1997, 8 pages.

PREPARATION OF CATIONIC SURFACTANTS

CROSS-REFERENCE TO RELATED APPLICATIONS

This application is a divisional of and claims the benefit of priority to U.S. patent application Ser. No. 16/942,565 filed on Jul. 29, 2020, the entire contents of which are incorporated by reference in its entirety.

TECHNICAL FIELD

This document relates to cationic surfactants and methods of preparation of cationic surfactants.

BACKGROUND

Surfactants are useful in many household and commercial applications. For example, new surfactants that are soluble and stable under harsh conditions would be useful in oil and gas recovery.

SUMMARY

This disclosure describes cationic surfactants composed of erucyl amidopropyl groups, with different head groups introduced by reaction with an epihalohydrin. This disclosure also describes one- and two-step methods of producing the cationic surfactants.

In some implementations, a composition includes a compound of Formula I:

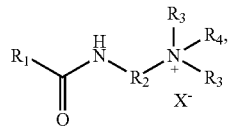

where X is halide, $R_1$ is a saturated or unsaturated alkyl with 4 to 28 carbons, $R_2$ is alkyl, $R_3$ is methyl, and $R_4$ is selected from the group consisting of

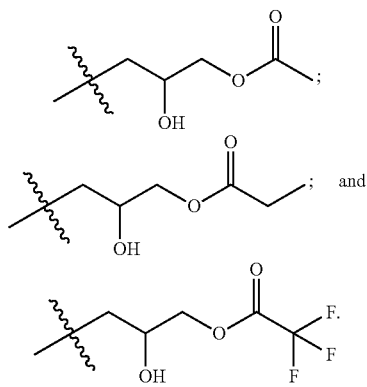

In some implementations, a composition includes a compound of Formula II:

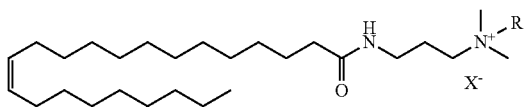

where R is selected from the group consisting of:

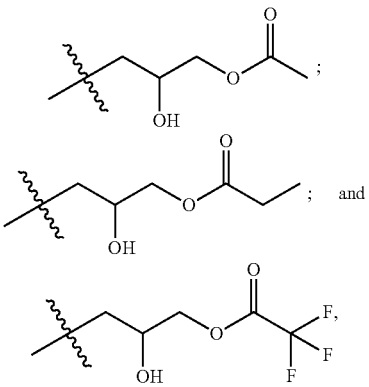

and where X is halide.

In some implementations, a process includes reacting a fatty acid modified with an amino alkyl group and an epihalohydrin, the presence of a base, to afford a cationic surfactant.

In some implementations, a process includes reacting a fatty acid modified with an amino alkyl group, an epihalohydrin, and a carboxylic acid to afford a cationic surfactant.

In some implementations, a process includes reacting a carboxylic acid, an epihalohydrin, and a catalyst to afford a halo-substituted alkyl ester. The process includes reacting the halo-substituted alkyl ester with a fatty acid modified with an amino alkyl group to afford a cationic surfactant. The details of one or more implementations of the disclosure are set forth in the accompanying drawings and the description that follows. Other features, objects, and advantages of the disclosure will be apparent from the description and drawings, and from the claims.

DESCRIPTION OF DRAWINGS

Like reference symbols in the various drawings indicate like elements.

DETAILED DESCRIPTION

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Provided in this disclosure, in part, are cationic surfactants and methods of producing cationic surfactants. These surfactants are useful in enhanced oil recovery applications. For example, many carbonate reservoirs have high temperatures and high brine salinity. Currently available surfactants and polymers have limited utility in these high temperature, high salinity formations. Accordingly, it is essential to develop new surfactants that are stable and useful at high temperature and high salinity situations. In addition, the surfactants with ultra-low interfacial tension, for example tension below $10^{-3}$ mN/m, are useful for releasing trapped oil in a reservoir. Accordingly, there is a need for surfactants that are stable at high temperature and high salinity formations that also display low or ultra-low interfacial tension with brine solutions.

Figure 1:
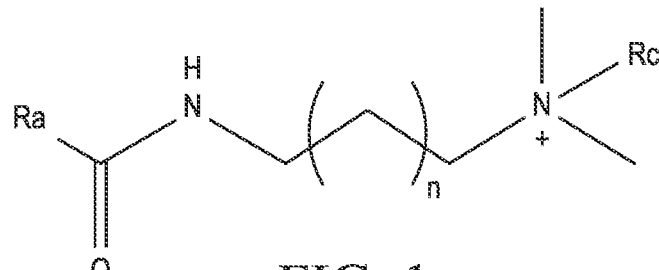
FIG. 1 shows an example structure of a cationic surfactant.

FIG. 1 shows the structure of an example cationic surfactant. In some implementations, the surfactants include a hydrophobic tail Ra, an alkyl spacer where n=1 to 6, and a cationic amine with two methyl groups and a functional group Rc. The resulting cationic surfactants, described in more detail below, are stable in high temperature and high salinity environments. Accordingly, these surfactants are useful in drilling and oil recovery applications, for example, for chemical flooding in a carbonate wellbore.

In some implementations, the hydrophobic tail Ra is derived from a saturated or unsaturated fatty acid with 4 to 28 carbons. The fatty acid tail can be branched, unbranched, saturated, or unsaturated in either a cis- or trans-configuration. The properties of the fatty acid tail can influence the properties of the surfactant, for example, by influencing the melting point, stability, solubility, or the critical micelle concentration of the surfactants in seawater.

In some implementations, the surfactants include ultra-long fatty acid chains, for example chains of 18 or more carbons. In some implementations, the fatty tail can be derived from erucic acid, a monounsaturated C22:1 ω9 fatty acid. Ultra-long fatty acid chains are very hydrophobic and typically not soluble in high salinity environments. However, the cationic surfactants described in this application have low interfacial tension and can be used in high salinity environments.

In some implementations, the fatty acid head group is modified with an alkyl spacer. For example, the carboxylic acid head group of a fatty acid can be reacted with an alkyl amine to form an amide bond between an alkyl spacer and a fatty acid. The alkyl spacer can be saturated alkyl group containing 1 to 6 carbons. For example, the spacer can be a propyl group. In some implementations, the spacer can include a tertiary amine functional group. This tertiary amine can be quaternized. For example, the reaction between a tertiary amine and an epihalohydrin results in a quaternary amine.

Quaternization of the tertiary amine introduces functional group Rc and results in the cationic surfactant. The positively charged amine of the cationic surfactant influences the solubility and stability of the surfactants. For example, in high-salinity environments the cation can reduce surfactant adsorption in carbonate reservoirs. The cation can also improve the stability of the surfactant at high salinity environments, for example in brines with high concentrations of divalent ions such as $Ca^{2+}$ and $Mg^{2+}$.

Quaternization of the tertiary amine can be achieved by a reaction with an epihalohydrin. For example, epichlorohydrin can quaternized the tertiary amine. Other epihalohydrins can also quaternized the tertiary amine. This results in an amine functionalized with an epoxy group. Under basic conditions, the epoxy can hydrolyze, yielding a dihydroxy functional group.

Figure 2:
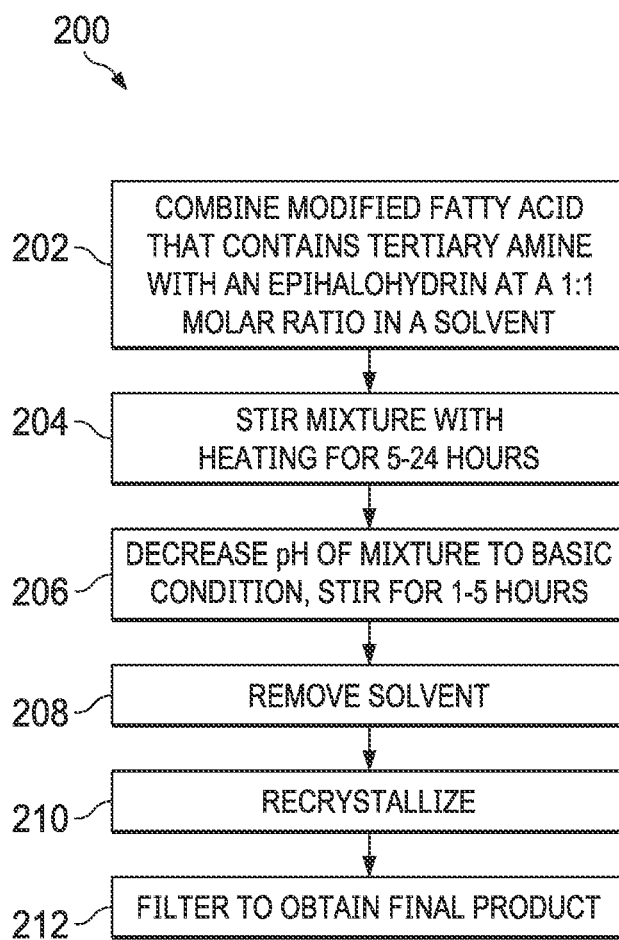
FIG. 2 is a flow chart of an example method for the quaternization of a tertiary amine.

FIG. 2 shows an example flow chart of a reaction scheme 200 for quaternization of a modified fatty acid. At 202, a fatty acid modified with a tertiary amine is combined with an epihalohydrin in a 1:1 molar ratio in a solvent. Suitable epihalohydrins include epichlorohydrin. At 204, the mixture is stirred, with heating, for 5-24 hours. At 206, the pH of the mixture is decreased to induce a basic condition. At 208, the solvent is removed from the mixture. At 210, the product is recrystallized. At 212, the final product is obtained by filtration.

Figure 3:
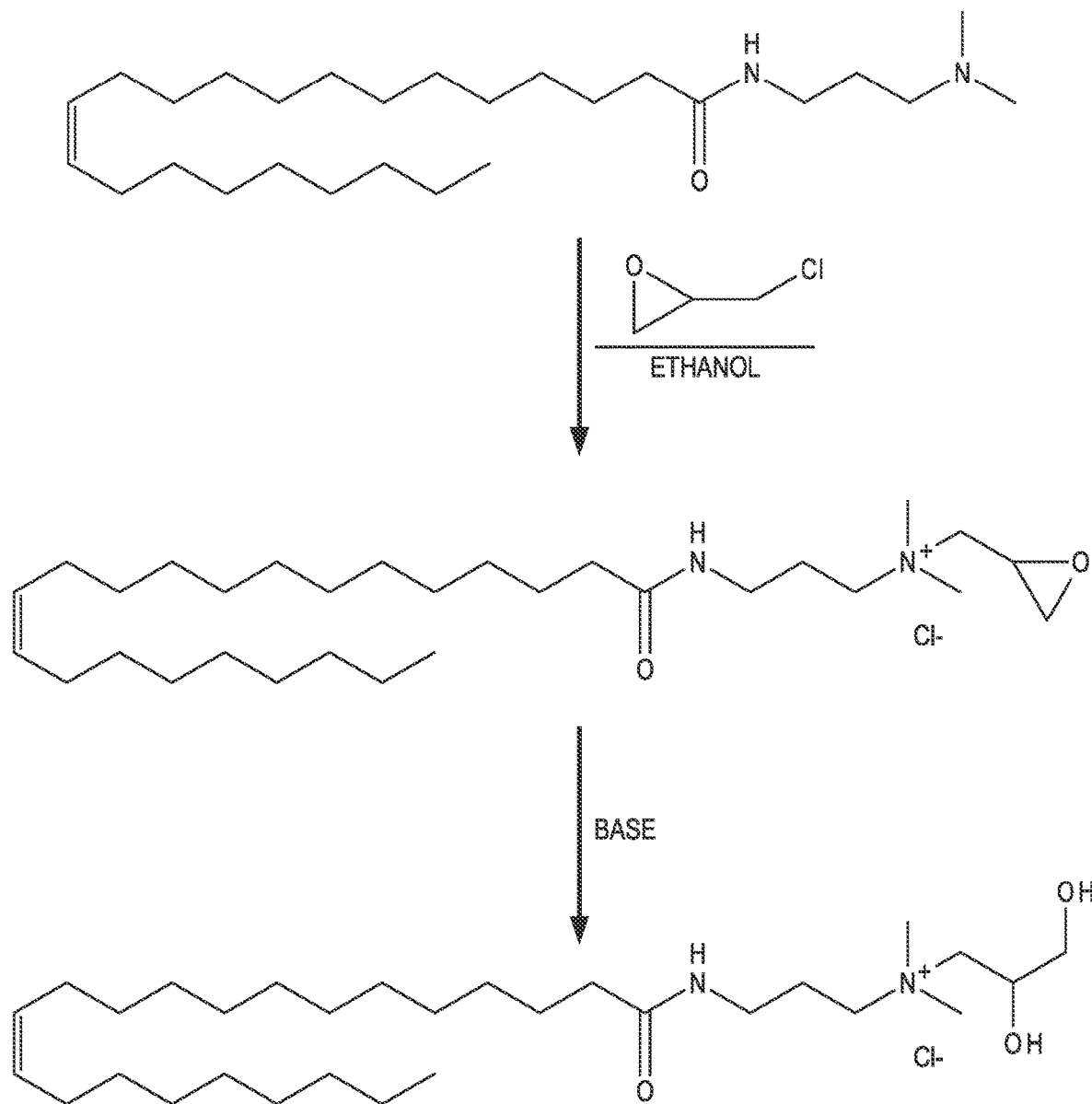
FIG. 3 is an example reaction of N, N-dimethyl-erucyl-1,3-propylenediamine with epichlorohydrin.

An example of the reaction scheme 200 is shown in FIG. 3, where N, N-dimethyl-erucyl-1,3-propylenediamine is reacted with epichlorohydrin. This functionalizes the quaternary amine with an epoxide. Under basic conditions, the epoxide can hydrolyze, yielding a 1,2-dihydroxylpropyl functional group. Recrystallization of the product results in the cationic surfactant erucyl amidopropyl-2,3-dihydroxypropyl ammonium chloride.

Figure 4:
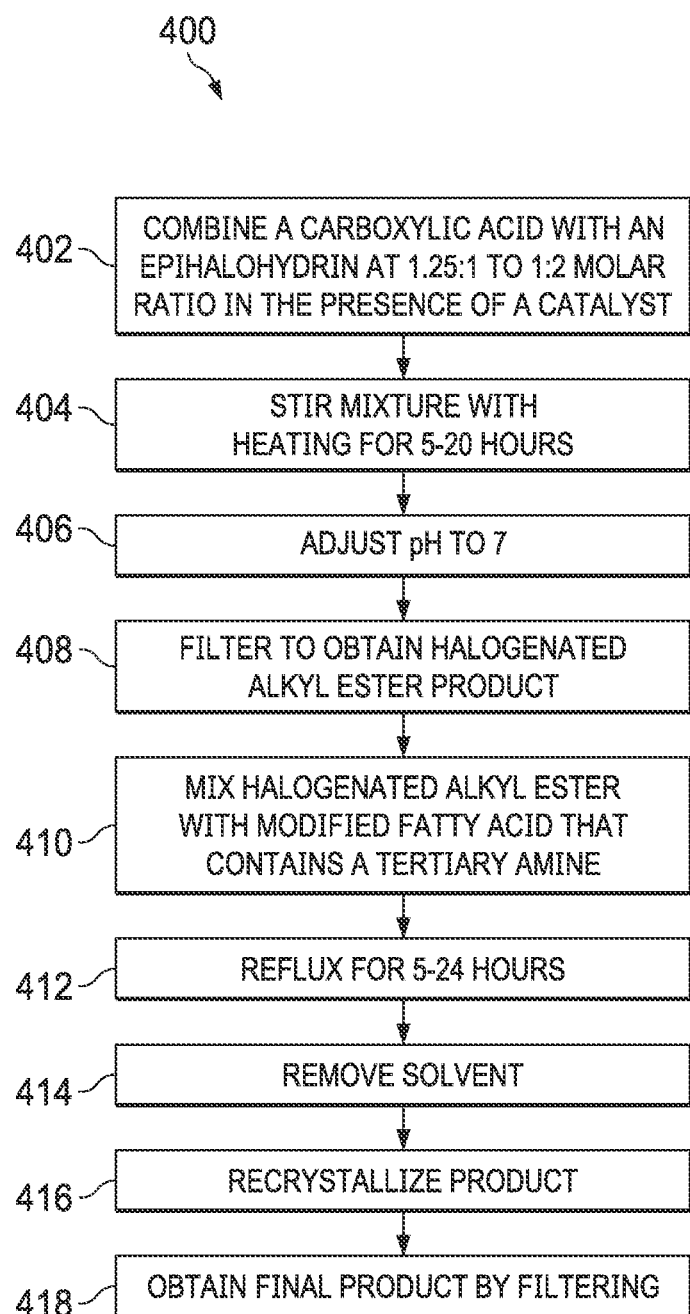
FIG. 4 is a flow chart of an example method of a two-step synthesis of cationic surfactants.

Cationic surfactants can also be synthesized using a two-step process 400. FIG. 4 shows an example flow chart of a reaction scheme 400 to synthesize cationic surfactants. At 402, a carboxylic acid is combined with an epihalohydrin at a 1.25:1 to 2:1 molar ratio in the presence of a catalyst. The choice of carboxylic acid can be used to introduce additional functional groups, such as hydroxyl, ester, or polymerizable groups such as a vinyl double bond. At 404, the mixture is stirred with heating for 5-20 hours. At 406, the pH of the mixture is adjusted to approximately 7. At 408, the mixture is filtered to obtain the halogenated alkyl ester product. At 410, the halogenated alkyl ester is mixed with a modified fatty acid that contains a tertiary amine. At 412, the mixture is refluxed for 5-24 hours. At 414, the solvent is removed. At 416, the product is recrystallized. At 418, the final product, the cationic surfactant, is obtained by filtering.

Figure 5A:
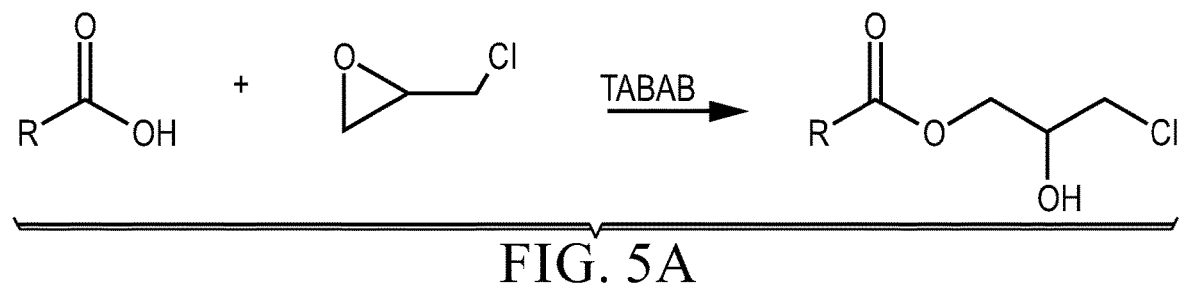
FIG. 5A is an example reaction of a carboxylic acid and epichlorohydrin, catalyzed by tetrabutylammonium bromide.
Figure 5B:
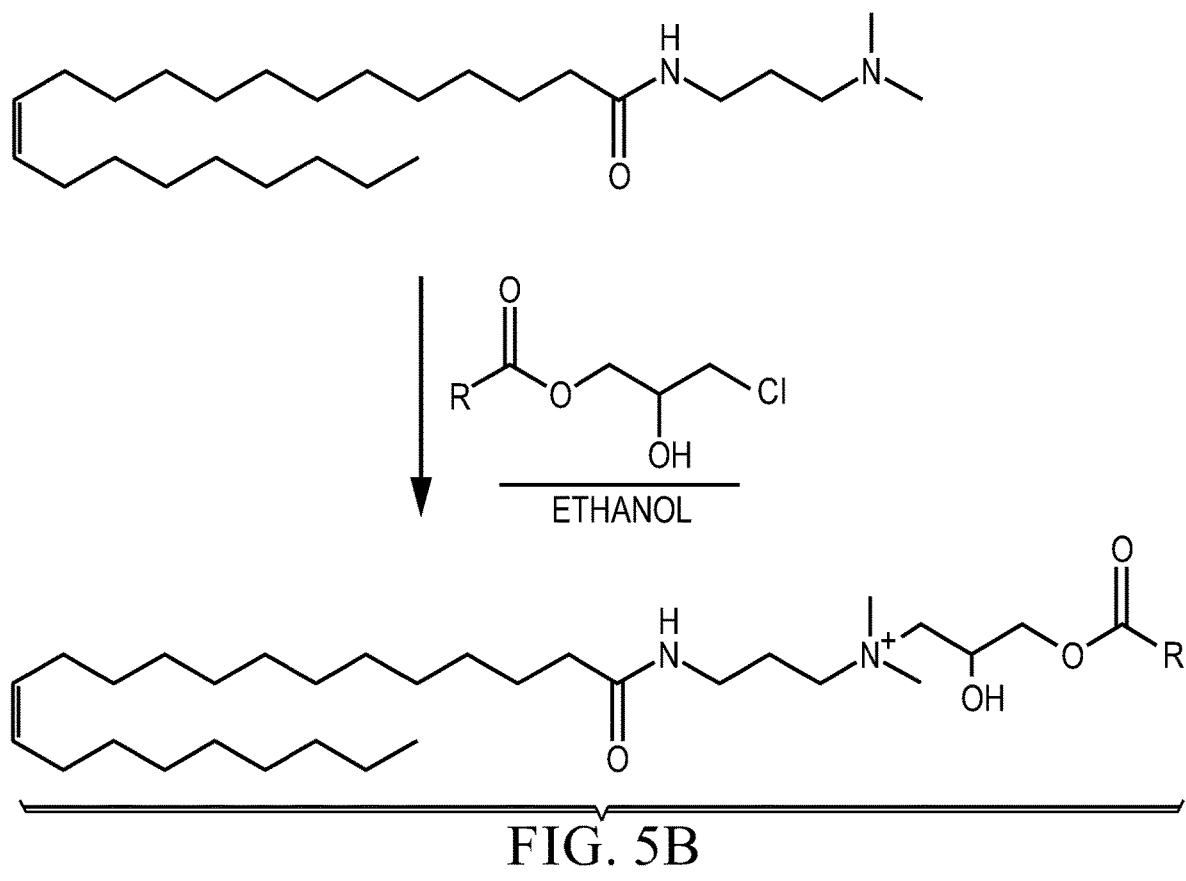
FIG. 5B is an example reaction of N,N-dimethyl-erucyl-1,3,-propylenediamine with the chloro-hydroxyl alkyl ester synthesized in FIG. 5A.

FIG. 5A shows an example reaction of the first step of the two-step process 400 between a carboxylic acid (COOR) and epichlorohydrin, catalyzed by tetrabutylammonium bromide (TBAB). Suitable carboxylic acids include, but are not limited to, acetic acid (R=—$CH_3$), trifluoroacetic acid (R=-$CF_3$), and propionic acid (R=—$CH_2$—$CH_3$). FIG. 5B shows an example reaction of the second step of the two-step process 400, where N,N-dimethyl-erucyl-1,3,-propylenediamine is combined with the chloro-hydroxyl alkyl ester synthesized in FIG. 5A. This generates a cationic surfactant that is compatible with brine solutions and has low oil-brine interfacial tension.

Figure 6:
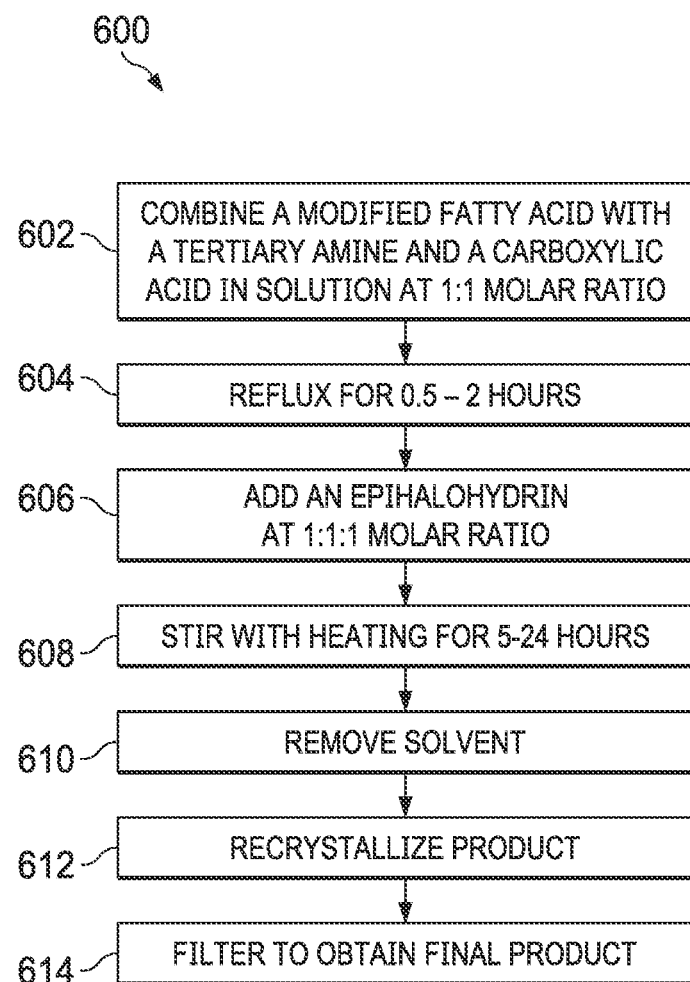
FIG. 6 is a flow chart of an example method of a one-step synthesis of cationic surfactants.
Figure 7:
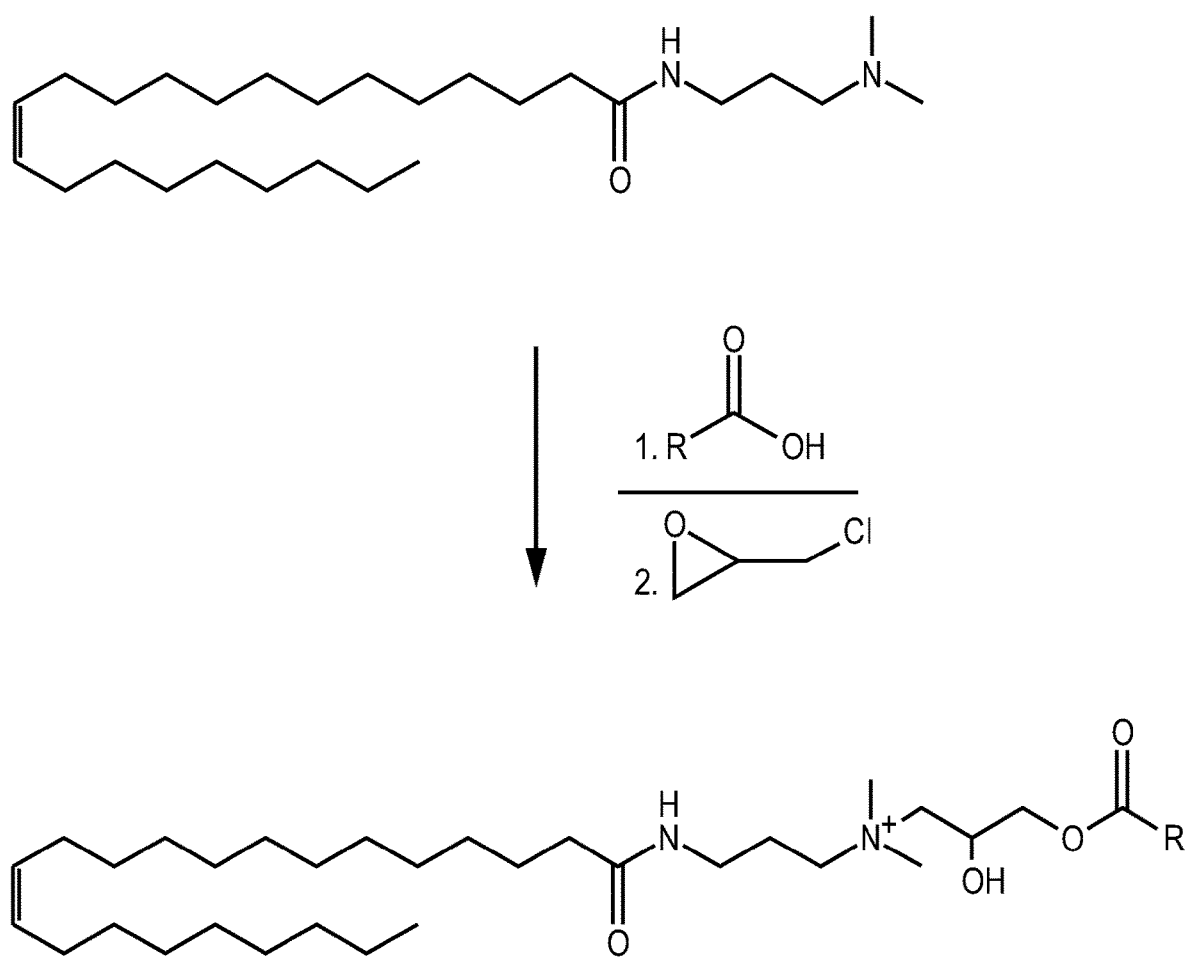
FIG. 7 is an example reaction of N,N-dimethylerucyl-1,3,-propylenediamine, a carboxylic acid, and epichlorohydrin.

In some implementations, the cationic surfactants can be synthesized using a one-step process. In the one-step process, a carboxylic acid, an epihalohydrin, and an alkyl-modified fatty acid containing a tertiary amine are reacted to generate the cationic surfactant. FIG. 6 shows an example flow chart of a reaction scheme 600 for a one-step synthesis of cationic surfactants. At 602, a modified fatty acid that contains a tertiary amine is combined in solution with a carboxylic acid in a 1:1 molar ratio. At 604, the mixture is refluxed for 0.5-2 hours. At 606, an epihalohydrin is added to the mixture, in a 1:1:1 ratio with the modified fatty acid and carboxylic acid. At 608, the mixture is stirred with heating for 5-24 hours. At 610, the solvent is removed. At 612, the product is recrystallized. At 614, the final product, the cationic surfactant, is obtained by filtering. FIG. 7 shows an example reaction of the one-step process 600, where N,N-dimethylerucyl-1,3,-propylenediamine is combined with a carboxylic acid and epichlorohydrin to yield the cationic surfactant. Suitable carboxylic acids include, but are not limited to, acetic acid (R=—$CH_3$), trifluoroacetic acid (R=—$CF_3$), and propionic acid (R=—$CH_2$—$CH_3$).

EXAMPLES

Tables 1 and 2 summarize the reactants for the one- and two-step synthetic processes, described in more detail below.

TABLE 1

Summary of One-Step Processes, Examples 1, 3, 5, and 7

| | Example | | | |
|---|---|---|---|---|
| | 1 | 3 | 5 | 7 |
| modified fatty acid | N, N-dimethyl-erucyl-1, 3-propylenediamine | N, N-dimethyl-erucyl-1, 3-propylenediamine | N, N-dimethyl-erucyl-1, 3-propylenediamine | N, N-dimethyl-erucyl-1, 3-propylenediamine |
| epoxide | epichlorohydrin | epichlorohydrin | epichlorohydrin | epichlorohydrin |
| carboxylic acid | none-base to open epichlorohydrin ring | acetic acid | trifluoroacetic acid | propionic acid |

TABLE 2

Summary of Two-Step Processes, Examples 2, 4, and 6

| | Example | | |
|---|---|---|---|
| | 2 | 4 | 6 |
| carboxylic acid | acetic acid | trifluoroacetic acid | propionic acid |
| epoxide | epichlorohydrin | epichlorohydrin | epichlorohydrin |
| catalyst | TBAB | TBAB | TBAB |
| fatty acid | N, N-dimethyl-erucyl-1, 3-propylenediamine | N, N-dimethyl-erucyl-1, 3-propylenediamine | N, N-dimethyl-erucyl-1, 3-propylenediamine |

Example 1

Synthesis of dihydroxyl Group: Erucyl amidopropyl-2, 3-dihydroxypropyl ammonium chloride ($C_{22}APDAC$)

50 mmol of N, N-dimethyl-erucyl-1, 3-propylenediamine and 55 mmol of epichlorohydrin were dissolved in 30 mL of ethanol. The mixture was stirred at 65° C. for 7 hours. Next, 50 mmol of NaOH was added to the mixture by adding 6.67 ml of 30 wt % NaOH solution, and the mixture was continuously stirred for 3 hours. After 3 hours, the ethanol solvent was removed under reduced pressure. The synthesized product was recrystallized in acetone and refrigerated at −15° C. for 48 hours. Following refrigeration, a light yellow paste was obtained by filtering. The yield of erucyl amidopropyl-2-hydroxy-3-acetoxypropyl ammonium chloride ($C_{22}APDAC$) was 76.1% by weight.

Figure 8:
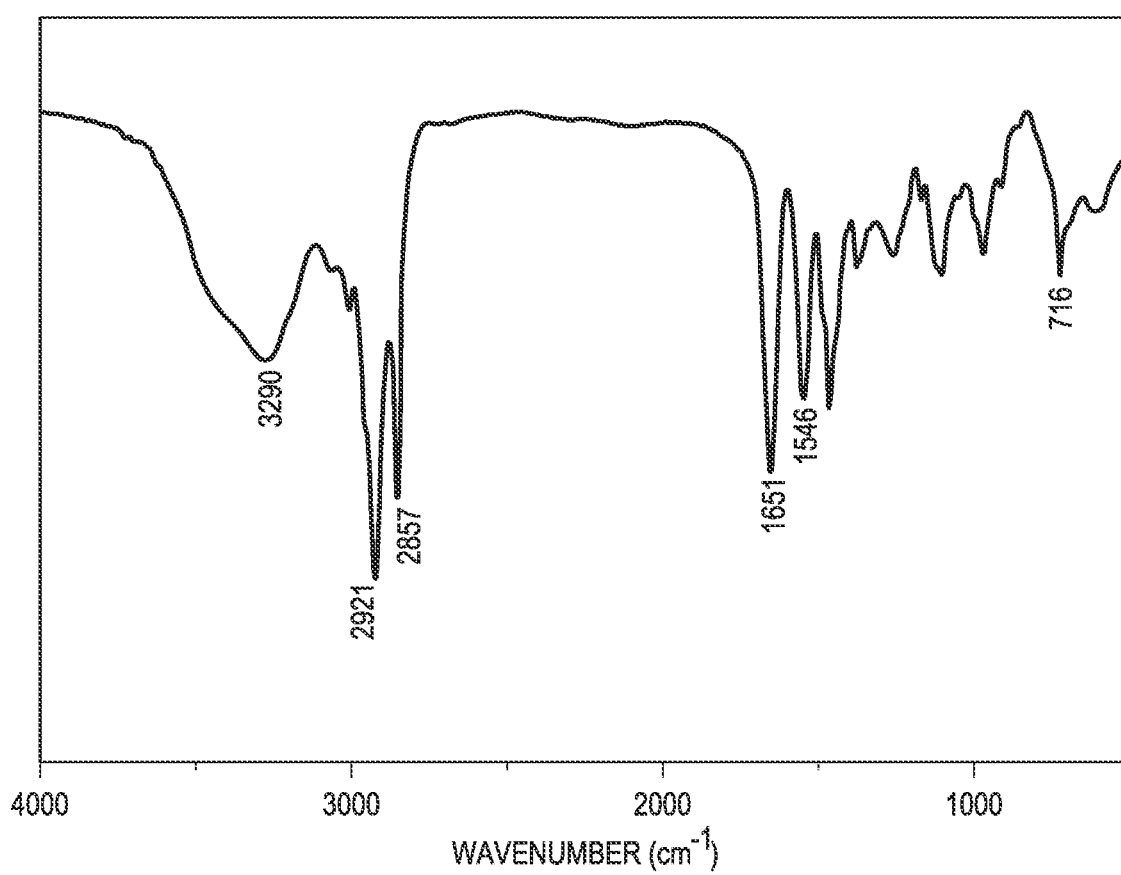
FIG. 8 is an example IR spectrum of erucyl amidopropyl-2,3-dihydroxypropyl ammonium chloride.

FIG. 8 shows an example infrared (IR) spectrum of $C_{22}APDAC$, confirming the structure of $C_{22}APDAC$ as synthesized in Example 1. The wide absorption at 3290 $cm^{-1}$ is due to the —N—H stretching vibration and the —O—H stretching vibration. The peaks at 2921 $cm^{-1}$ and 2857 $cm^{-1}$ are the stretching vibrations of the —$CH_3$ and —C—H—(—$CH_2$—) groups, respectively. The peak at 1651 $cm^{-1}$ is the —C=O stretching vibration of the amide group. The peak at 716 $cm^{-1}$ indicates the existence of the alkyl chain. Accordingly, the IR spectrum in FIG. 8 confirms the structure of $C_{22}APDAC$.

Figure 9:
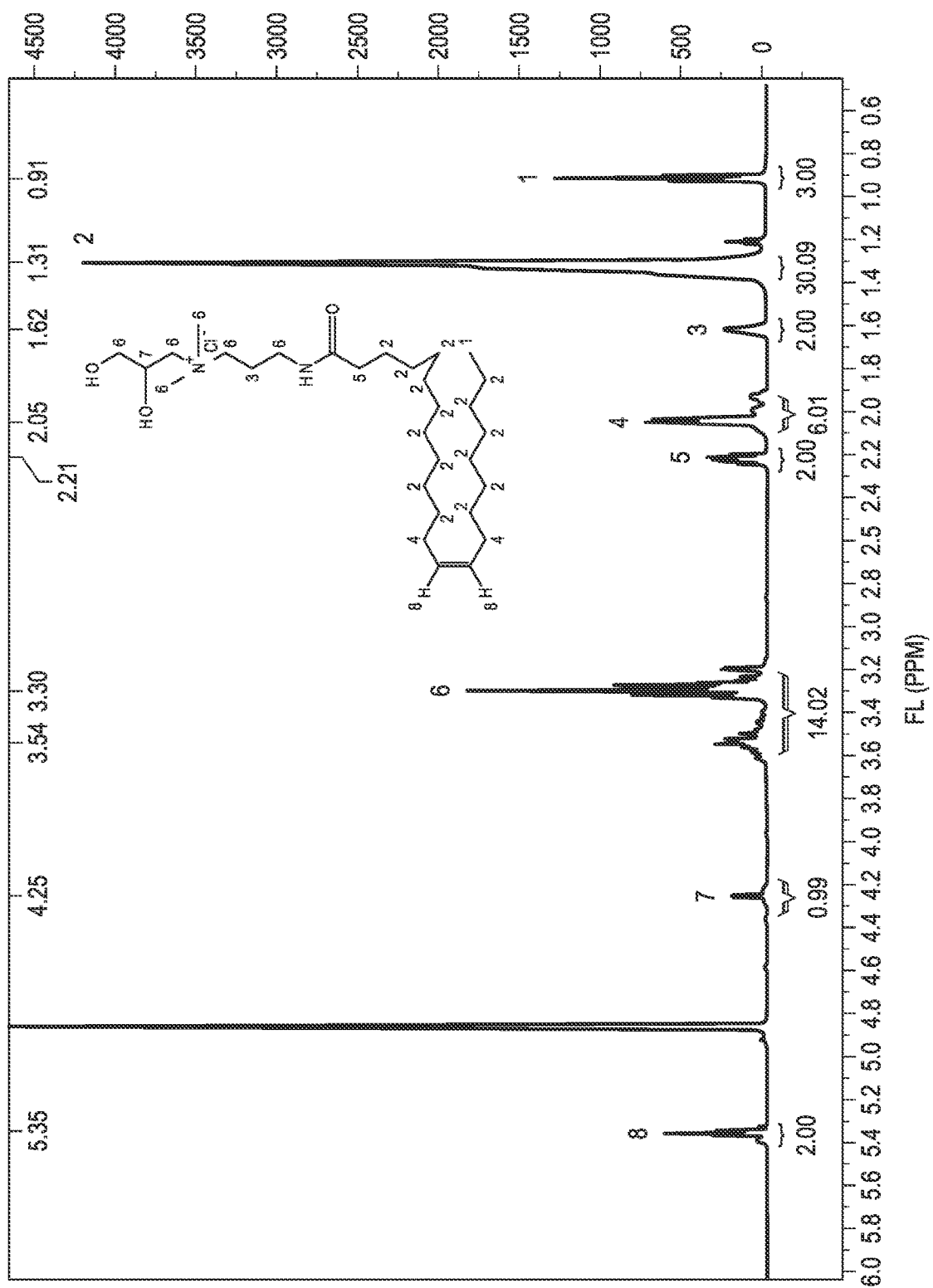
FIG. 9 is an example $^1$HNMR spectrum of erucyl amidopropyl-2,3-dihydroxypropyl ammonium chloride.

FIG. 9 is an example $^1HNMR$ spectrum of $C_{22}APDAC$, confirming the structure of $C_{22}APDAC$ as synthesized in Example 1. $C_{22}APDAC$ was analyzed at 400 MHz in deuterated methanol. The following spectral peaks were observed, wherein s is a singlet, t is a triple, and m is a multiplet: 0.91 (m, 3H, 1), 1.31 (s, 30H, 2), 1.62 (s, 2H, 3), 2.05 (m, 6H, 4), 2.21 (m, 2H, 5), 3.30 (m, 14H, 6), 4.25 (m, H, 7), 5.35 (t, 2H, 8). The $^1HNMR$ spectrum provides additional confirmation of the structure of $C_{22}APDAc$.

Example 2

Two-Step Synthesis of erucyl amidopropyl-2-hydroxy-3-acetoxypropyl ammonium chloride ($C_{22}APHAAC$)

250 mmol of acetic acid, 200 mmol of epichlorohydrin, and 6.25 mmol of tetrabutylammonium bromide (TBAB) were combined. The reaction mixture was heated to 90° C. with stirring for 10 hours. After the reaction, the mixture was washed with saturated NaCl solution until the pH of the mixture was around 7. The remaining water in the mixture was removed using $Na_2SO_4$. The product was recovered by filtering the solid. The yield of 3-chloro-2-hydroxypropyl acetate was about 65% by weight.

25 mmol of N, N-dimethyl-erucyl-1, 3-propylenediamine and 30 mmol of 3-chloro-2-hydroxypropyl alkyl ester were dissolved in 30 mL ethanol. The mixture was refluxed at 65° C. for 10 hours. The solvent was then removed under reduced pressure using a rotary evaporator. The synthesized product was recrystallized with acetone and refrigerated at −15° C. for 48 hours. Following refrigeration, a light yellow paste was obtained by filtering the solution. The yield of the ester cationic surfactant erucyl amidopropyl-2-hydroxy-3-acetoxypropyl ammonium chloride ($C_{22}APHAAC$) was 82.5% by weight.

Example 3

One-Step Synthesis of Erucyl amidopropyl-2-hydroxy-3-acetoxypropyl ammonium chloride ($C_{22}APHAAC$)

50 mmol of N, N-dimethyl-erucyl-1, 3-propylenediamine was mixed with 50 mmol of acetic acid in 10 mL of isopropanol. The mixture was heated to 95° C. for 0.5 hours. 60 mmol of epichlorohydrin was added to the mixture. The mixture was then refluxed at 95° C. for 7 hours. The solvent was removed under reduced pressure to yield a yellow, oily product. The synthesized product was recrystallized with acetone at −15° C. for 24 hours. The purified product was obtained by filtering. The yield of the ester cationic surfactant $C_{22}APHAAC$ was 84.85% by weight.

Figure 10:
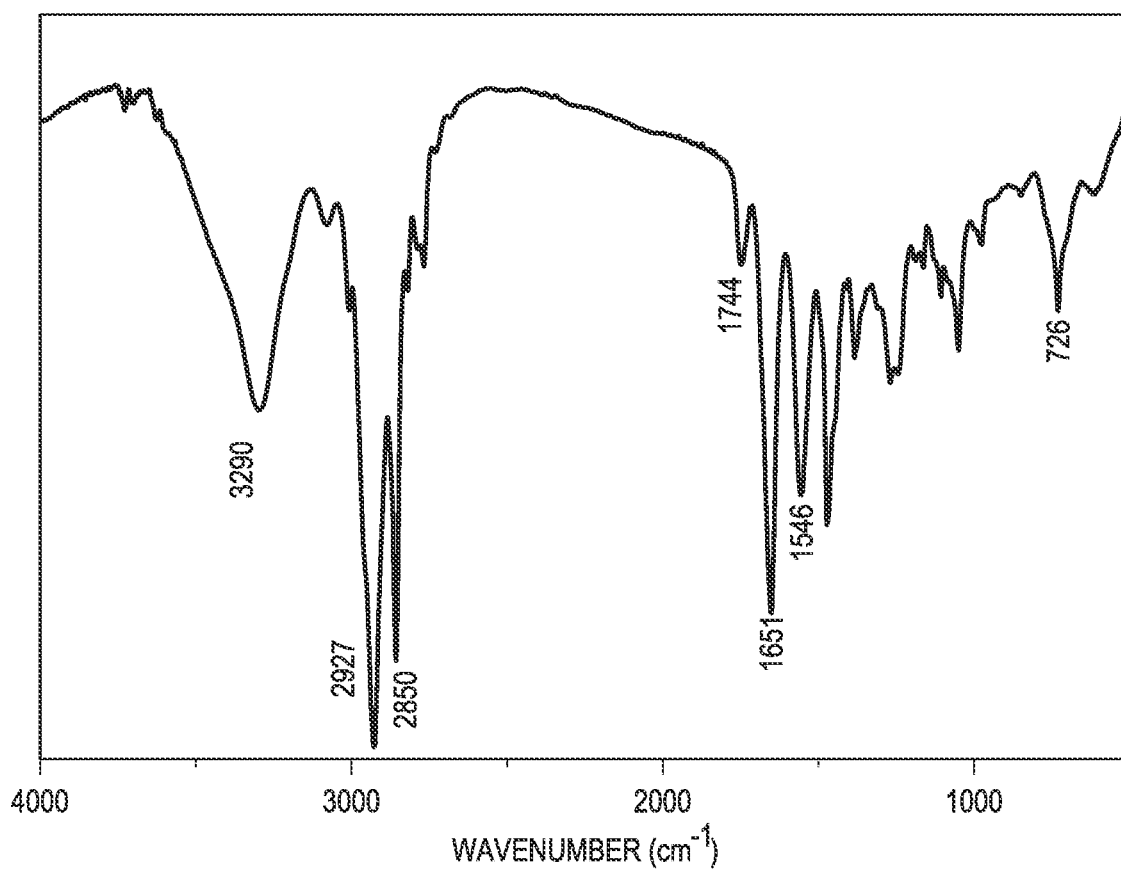
FIG. 10 is an example IR spectrum of erucyl amidopropyl-2-hydroxy-3-acetoxypropyl ammonium chloride.

FIG. 10 shows an example IR spectrum of $C_{22}APHAAC$, confirming the structure of $C_{22}APHAAC$ as synthesized in Example 3. The wide absorption at 3290 $cm^{-1}$ is due to the N—H stretching vibration and the —O—H stretching vibration. The peaks at 2927 $cm^{-1}$ and 2850 $cm^{-1}$ are considered to be the stretching vibration of —$CH_3$ and —C—H—($CH_2$—) groups. The peak at 1744 $cm^{-1}$ is considered to be the —C=O stretching vibration of the ester group and the peak at 1651 $cm^{-1}$ is considered to be the —C=O stretching vibration of the amide group. The peak at 726 $cm^{-1}$ indicates the existence of the alkyl chain. Accordingly, the IR spectrum confirms the structure of $C_{22}APHAAC$ as synthesized in Example 3.

Figure 11:
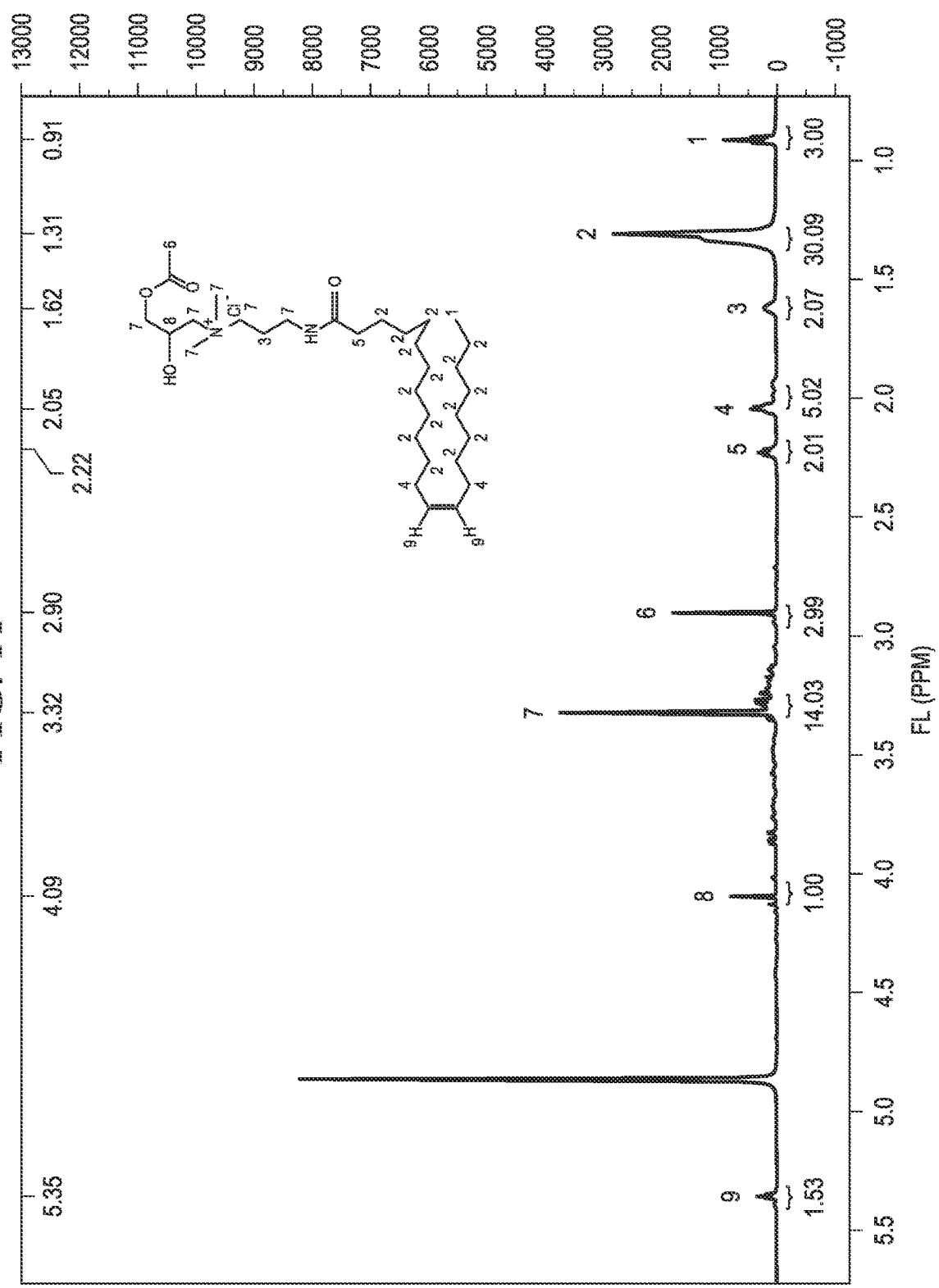
FIG. 11 is an example $^1$HNMR spectrum of erucyl amidopropyl-2-hydroxy-3-acetoxypropyl ammonium chloride.

FIG. 11 shows an example $^1HNMR$ spectrum of $C_{22}APHAAC$, confirming the structure of $C_{22}APHAAC$ as synthesized in Example 3. $C_{22}APHAAC$ was analyzed at 400 MHz in deuterated methanol. The following spectral peaks were observed, wherein s is a singlet, t is a triple, and m is a multiplet: 0.91 (m, 3H, 1), 1.31 (s, 30H, 2), 1.62 (s, 2H, 3), 2.05 (m, 5H, 4), 2.22 (m, 2H, 5), 2.90 (m, 3H, 6), 3.32 (m, 14H, 7), 4.09 (t, 1H, 8), 5.35 (t, 2H, 9). The $^1HNMR$ spectrum provides additional confirmation of the structure of $C_{22}APHAAC$.

Example 4

Two-Step Synthesis of Erucyl amidopropyl-2-hydroxy-3-(2,2,2 trifluoroacetoxy) propyl ammonium chloride ($C_{22}APHFAC$)

$C_{22}APHFAC$ was prepared with the same two-step method as Example 2, except with trifluoroacetic acid instead of acetic acid. 250 mmol of trifluoroacetic acid, 200 mmol of epichlorohydrin, and 6.25 mmol of tetrabutylammonium bromide (TBAB) were combined. The reaction mixture was heated to 90° C. with stirring for 10 hours. After the reaction, the mixture was washed with saturated NaCl solution until the pH of the mixture was around 7. The remaining water in the mixture was removed using Na2SO4. The product was recovered by filtering the solid. The yield of 3-chloro-2-hydroxypropyl 2, 2, 2-trifluoroacetate was 70% by weight.

25 mmol of N, N-dimethyl-erucyl-1, 3-propylenediamine and 30 mmol of 3-chloro-2-hydroxypropyl 2, 2, 2-trifluoroacetate were dissolved in 30 mL ethanol. The mixture was refluxed at 65° C. for 10 hours. The solvent was then removed under reduced pressure. The synthesized product was recrystallized with acetone and refrigerated at −15° C.

for 48 hours. A light yellow paste was obtained by filtering the solution. The yield of the ester cationic surfactant $C_{22}$APHFAC was 82.5%.

Example 5

One-Step Synthesis of Erucyl amidopropyl-2-hydroxy-3-(2, 2, 2-trifluoroacetoxy) propyl ammonium chloride ($C_{22}$APHFAC)

$C_{22}$APHFAC was prepared by a one-step method with the same procedures as Example 3, except trifluoroacetic acid was used instead of acetic acid. 50 mmol of N, N-dimethyl-erucyl-1, 3-propylenediamine was mixed with 50 mmol of trifluoroacetic acid in 10 mL of isopropanol. The mixture was heated to 95° C. for 0.5 hours. 60 mmol of epichlorohydrin was added to the mixture. The mixture was then refluxed at 95° C. for 7 hours. The solvent was removed under reduced pressure. The synthesized product was recrystallized with acetone at −15° C. for 24 hours. The purified product was obtained by filtering. The yield of the ester cationic surfactant $C_{22}$APFAC was 70% by weight.

Figure 12:
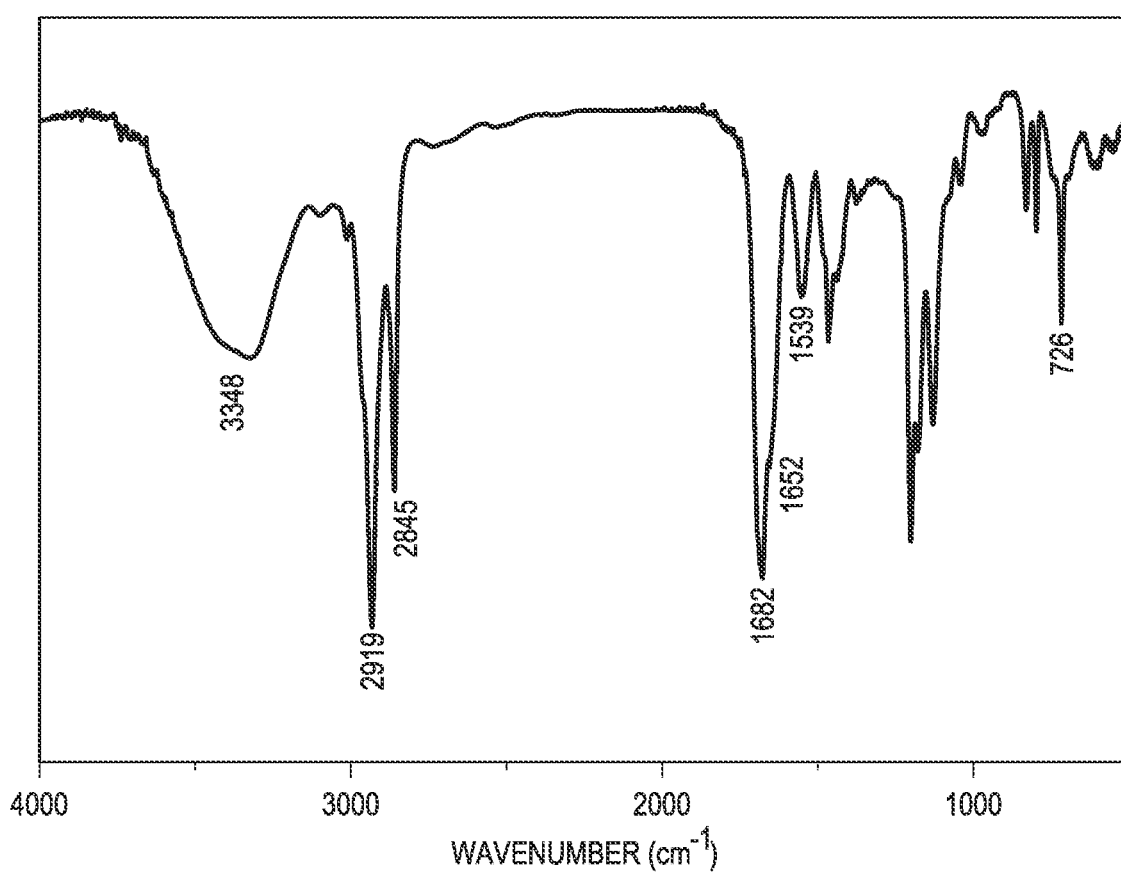
FIG. 12 is an example IR spectrum of erucyl amidopropyl-2-hydroxy-3-(2, 2, 2-trifluoroacetoxy) propyl ammonium chloride.

FIG. 12 shows an example IR spectrum of $C_{22}$APFAC, as synthesized in Example 5. The IR spectrum shows a wide absorption at 3348 cm$^{-1}$ due to the —N—H stretching vibration and the —O—H stretching vibration. The peaks at 2919 cm$^{-1}$ and 2845 cm$^{-1}$ are considered to be the stretching vibrations of —CH$_3$ and —C—H (—CH$_2$—) groups. The peak at 1682 cm$^{-1}$ is considered to be the —C═O stretching vibration of the ester group and the peak at 1652 cm$^{-1}$ is considered to be the —C═O stretching of the amide group. The peak at 726 cm$^{-1}$ indicates the existence of the alkyl chain. Accordingly, the IR spectrum confirms the structure of $C_{22}$APFAC.

Figure 13:
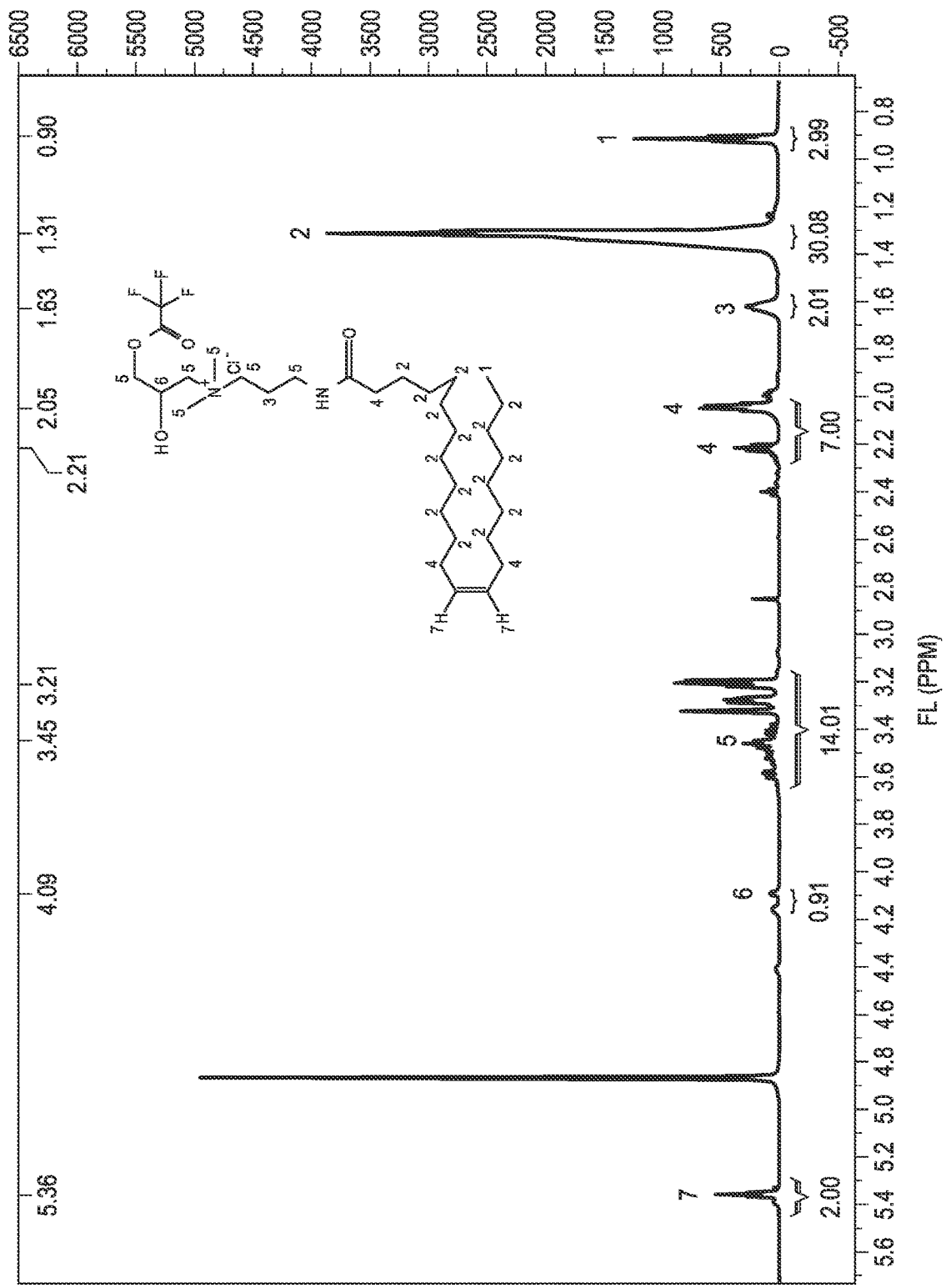
FIG. 13 is an example $^1$HNMR spectrum of erucyl amidopropyl-2-hydroxy-3-(2, 2, 2-trifluoroacetoxy) propyl ammonium chloride.

FIG. 13 shows an example $^1$HNMR spectrum, confirming the structure of $C_{22}$APFAC as synthesized in Example 5. $C_{22}$APFAC was analyzed at 400 MHz in deuterated methanol. The following spectral peaks were observed, wherein s is a singlet, t is a triple, and m is a multiplet: 0.90 (m, 3H, 1), 1.31 (s, 30H, 2), 1.63 (s, 2H, 3), 2.05 (m, 7H, 4), 3.21 (m, 14H, 5), 4.09 (t, 1H, 6), 5.36 (t, 2H, 7). The $^1$HNMR spectrum provides additional confirmation of the structure of $C_{22}$APFAC.

Example 6

Two-Step Synthesis of Erucyl amidopropyl-2-hydroxy-3-propoionyloxy propyl ammonium chloride ($C_{22}$APHPAC)

$C_{22}$APHPAC was prepared by a two-step method with the same procedures as example 2, except using propionic acid instead of acetic acid. 250 mmol of propionic acid, 200 mmol of epichlorohydrin, and 6.25 mmol of tetrabutylammonium bromide (TBAB) were combined. The reaction mixture was heated to 90° C. with stirring for 10 hours. After the reaction, the mixture was washed with saturated NaCl solution until the pH of the mixture was around 7. The remaining water in the mixture was removed using Na$_2$SO$_4$. The product was recovered by filtering the solid. The yield of 3-chloro-2-hydroxypropyl propionate was 50% by weight.

25 mmol of N, N-dimethyl-erucyl-1, 3-propylenediamine and 30 mmol of 3-chloro-2-hydroxypropyl propionate were dissolved in 30 mL ethanol. The mixture was refluxed at 65° C. for 10 hours. The solvent was then removed under reduced pressure. The synthesized product was recrystallized with acetone and refrigerated at −15° C. for 48 hours. The product was obtained by filtering the solution. The yield of $C_{22}$APHPAC was 53%.

Example 7

One-Step Synthesis of Erucyl amidopropyl-2-hydroxy-3-propionyloxy propyl ammonium chloride ($C_{22}$APHPAC)

$C_{22}$APHPAC was prepared by a one-step method with the same procedures as Example 3, except that propionic acid was used in place of acetic acid. 50 mmol of N, N-dimethyl-erucyl-1, 3-propylenediamine was mixed with 50 mmol of propionic acid in 10 mL of isopropanol. The mixture was heated to 95° C. for 0.5 hours. 60 mmol of epichlorohydrin was added to the mixture. The mixture was then refluxed at 95° C. for 7 hours. The solvent was removed under reduced pressure. The synthesized product was recrystallized with acetone at −15° C. for 24 hours. The purified product was obtained by filtering. The yield of the cationic surfactant $C_{22}$APHPAC was 54%.

Figure 14:
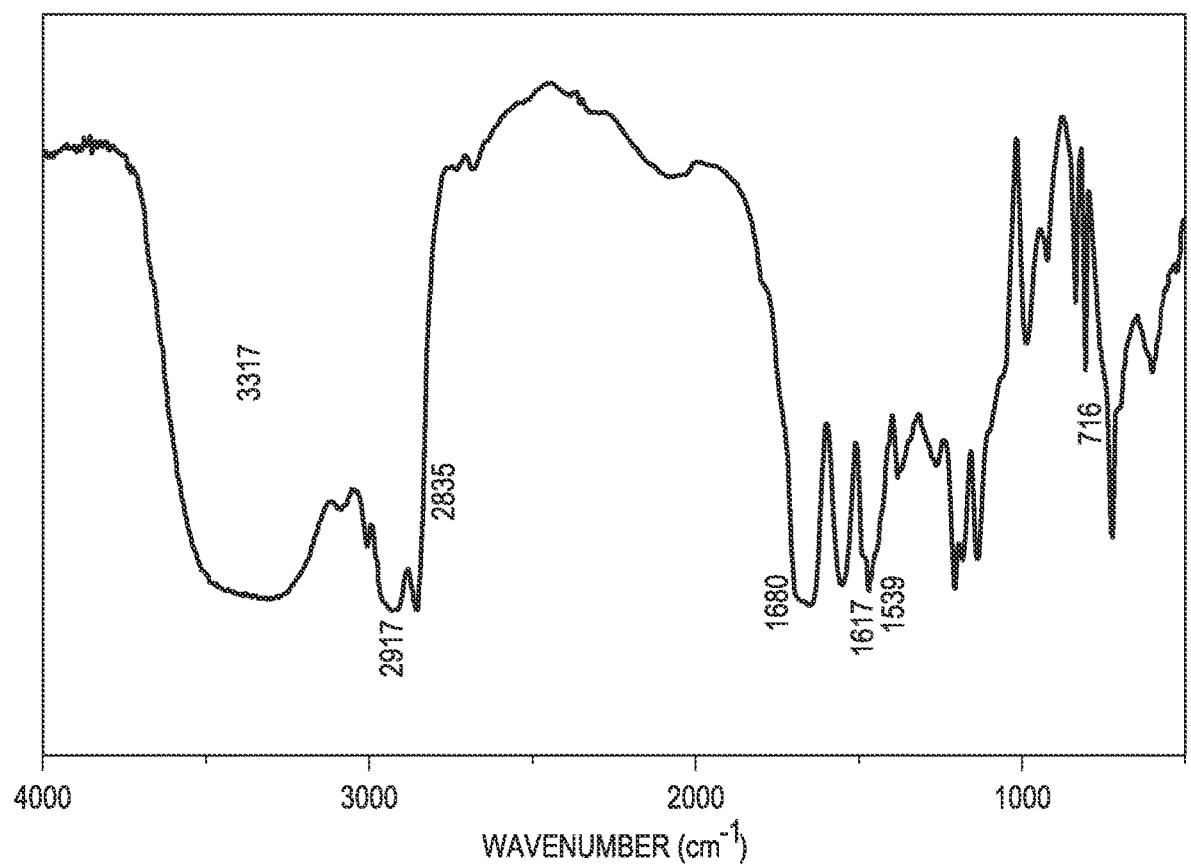
FIG. 14 is an example IR spectrum of erucyl amidopropyl-2-hydroxy-3-propionyloxy propyl ammonium chloride.

FIG. 14 shows an example IR spectrum of $C_{22}$APHPAC as synthesized in Example 7. The wide absorption at 3317 cm$^{-1}$ is due to the —N—H stretching vibration and the —O—H stretching vibration. The peaks at 2917 cm$^{-1}$ and 2835 cm$^{-1}$ are considered to be the stretching vibrations of the —CH$_3$ and —C—H—(—CH$_2$—) groups, respectively. The peak at 1680 cm$^{-1}$ is considered to be the —C═O stretching vibration of the ester group, and the peak at 1617 cm$^{-1}$ is considered to be the —C═O stretching vibration of the amide group. The peak at 716 cm$^{-1}$ indicates the existence of the alkyl chain. Accordingly, the IR spectrum confirms the structure of $C_{22}$APHPAC.

Figure 15:
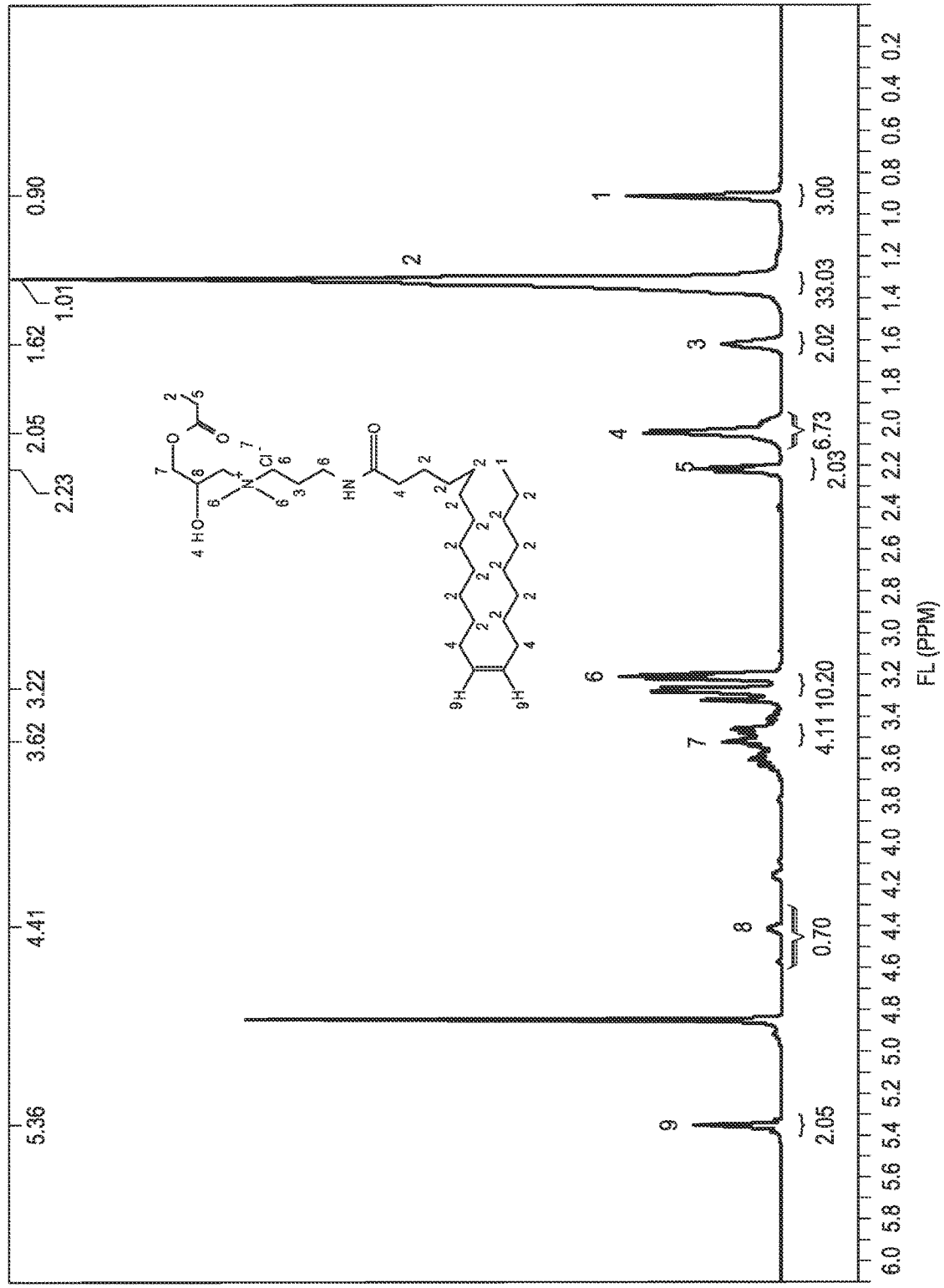
FIG. 15 is an example $^1$HNMR spectrum of erucyl amidopropyl-2-hydroxy-3-propionyloxy propyl ammonium chloride.

FIG. 15 shows an example $^1$HNMR spectrum, confirming the structure of $C_{22}$APHPAC as synthesized in Example 7. $C_{22}$APHPAC was analyzed at 400 MHz in deuterated methanol. The following spectral peaks were observed, wherein s is a singlet, t is triple, and m is multiplet: 0.91 (m, 3H, 1), 1.31 (s, 33H, 2), 1.62 (s, 2H, 3), 2.05 (m, 7H, 4), 2.23 (m, 2H, 5), 3.27 (m, 10H, 6), 3.52 (m, 4H, 7), 4.41 (t, 1H, 8), 5.36 (t, 2H, 9). The $^1$HNMR spectrum provides additional confirmation of the structure of $C_{22}$APHPAC.

Example 8: Properties of Product Surfactants

The properties of the surfactants in seawater including compatibility, critical micelle concentration (CMC) and the interfacial tension were investigated. The composition of seawater is listed in Table 3 and the observed properties of the surfactants are presented in Table 4.

TABLE 3

| | Chemical composition of seawater | | | | | | |
|---|---|---|---|---|---|---|---|
| | Cations | | | Anions | | | |
| Seawater | $Na^+$ | $Ca^{2+}$ | $Mg^{2+}$ | $Cl^-$ | $HCO_3^-$ | $SO_4^{2-}$ | Total salinity |
| Concentration (ppm) | 18,300 | 659 | 2,110 | 32,200 | 120 | 4,290 | 57,670 |

TABLE 4

| | Properties of surfactants | | | | | |
|---|---|---|---|---|---|---|
| | Compatibility[1] | | | IFT (mN/m) | | |
| Surfactant | 25° C. | 95° C. | CMC (mol/L) | 500 mg/L | 1000 mg/L | 2000 mg/L |
| $C_{22}APDAC$ | A | A | $9.58 \times 10^{-6}$ | $2.11 \times 10^{-4}$ | $1.21 \times 10^{-4}$ | $1.1 \times 10^{-3}$ |
| $C_{22}APHAAC$ | A | B | $1.09 \times 10^{-5}$ | 1.11 | $4.83 \times 10^{-3}$ | $2.37 \times 10^{-3}$ |
| $C_{22}APHFAC$ | A | B | $1.08 \times 10^{-5}$ | 0.31 | $1.87 \times 10^{-2}$ | $7.12 \times 10^{-3}$ |
| $C_{22}APHPAC$ | A | B | $1.25 \times 10^{-5}$ | $5.7 \times 10^{-2}$ | $7 \times 10^{-3}$ | $4.2 \times 10^{-2}$ |

[1] A = clear;
B = phase separation.

As shown in Table 4, the cationic surfactants synthesized in this disclosure have low interfacial tension and are soluble in high salinity environments. Low CMC values indicate the applicability of the surfactant at low concentrations. Accordingly, these solvents will be useful in a number of applications, including enhanced oil recovery.

The following units of measure have been mentioned in this disclosure:

| Unit of Measure | Full form |
|---|---|
| L | liter |
| mL | milliliter |
| mg | milligram |
| mmol | millimole |
| mN | milli Newtons |
| m | meter |
| ppm | parts per million |
| ° C. | degree Celsius |
| hr | hour |
| $cm^{-1}$ | inverse centimeter, wavenumber |
| MHz | megahertz |

In some implementations, a composition includes a compound of Formula I:

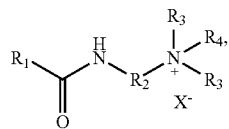

where X is halide, $R_1$ is a saturated or unsaturated alkyl with 4 to 28 carbons, $R_2$ is alkyl, $R_3$ is methyl, and $R_4$ is selected from the group consisting of

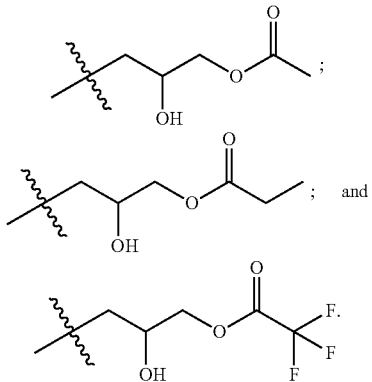

This aspect, taken alone or combinable with any other aspect, can include the following features. $R_2$ is propyl.

This aspect, taken alone or combinable with any other aspect, can include the following features. $R_1$ is a monounsaturated alkyl chain with 21 carbons.

This aspect, taken alone or combinable with any other aspect, can include the following features. $R_1$ is

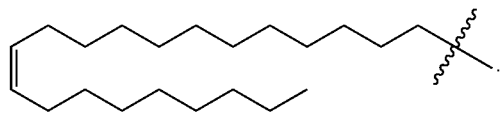 [SMILES: *CCCCCCCCCCC/C=C\CCCCCCCC]

This aspect, taken alone or combinable with any other aspect, can include the following features. $R_4$ is

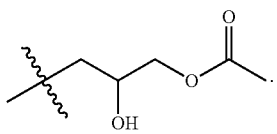 [SMILES: *CC(O)COC(C)=O]

This aspect, taken alone or combinable with any other aspect, can include the following features. $R_4$ is

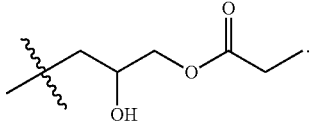 [SMILES: *CC(O)COC(=O)CC]

This aspect, taken alone or combinable with any other aspect, can include the following features. $R_4$ is

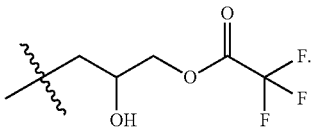 [SMILES: *CC(O)COC(=O)C(F)(F)F]

In some implementations, a composition includes a compound of Formula II:

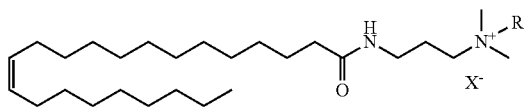

where R is selected from the group consisting of:

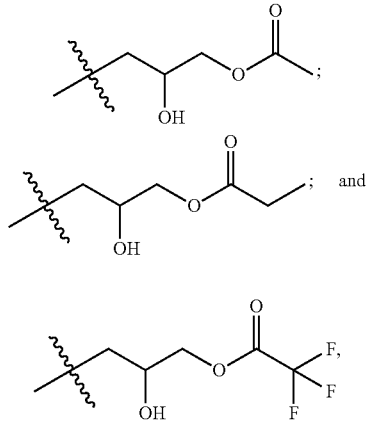

and where X is halide.

This aspect, taken alone or combinable with any other aspect, can include the following features. R is

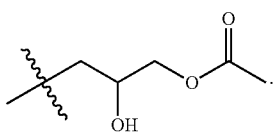 [SMILES: *CC(O)COC(C)=O]

This aspect, taken alone or combinable with any other aspect, can include the following features. R is

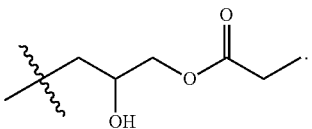 [SMILES: *CC(O)COC(=O)CC]

This aspect, taken alone or combinable with any other aspect, can include the following features. R is

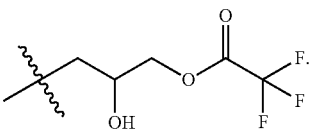 [SMILES: *CC(O)COC(=O)C(F)(F)F]

In some implementations, a process includes reacting a fatty acid modified with an amino alkyl group and an epihalohydrin, the presence of a base, to afford a cationic surfactant.

This aspect, taken alone or combinable with any other aspect, can include the following features. Reacting the fatty acid modified with an amino alkyl group includes reacting N, N-dimetyl-erucyl-1,3,-propylenediamine.

This aspect, taken alone or combinable with any other aspect, can include the following features. Reacting the epihalohydrin includes reacting epichlorohydrin.

This aspect, taken alone or combinable with any other aspect, can include the following features. Reacting in the presence of a base includes reacting in a presence of sodium hydroxide.

In some implementations, a process includes reacting a fatty acid modified with an amino alkyl group, an epihalohydrin, and a carboxylic acid to afford a cationic surfactant.

This aspect, taken alone or combinable with any other aspect, can include the following features. Reacting a fatty acid modified with an amino alkyl group includes reacting N,N-dimethyl-erucyl-1,3,-propylenediamine.

This aspect, taken alone or combinable with any other aspect, can include the following features. Reacting an epihalohydrin includes reacting epichlorohydrin.

This aspect, taken alone or combinable with any other aspect, can include the following features. Reacting a carboxylic acid includes reacting a carboxylic acid selected from acetic acid, propionic acid; and trifluoroacetic acid.

This aspect, taken alone or combinable with any other aspect, can include the following features. Reacting a carboxylic acid includes reacting acetic acid.

This aspect, taken alone or combinable with any other aspect, can include the following features. Reacting a carboxylic acid includes reacting propionic acid.

This aspect, taken alone or combinable with any other aspect, can include the following features. Reacting a carboxylic acid includes reacting trifluoroacetic acid.

In some implementations, a process includes reacting a carboxylic acid, an epihalohydrin, and a catalyst to afford a halo-substituted alkyl ester. The process includes reacting the halo-substituted alkyl ester with a fatty acid modified with an amino alkyl group to afford a cationic surfactant.

This aspect, taken alone or combinable with any other aspect, can include the following features. Reacting a catalyst includes reacting tetrabutylammonium bromide.

This aspect, taken alone or combinable with any other aspect, can include the following features. Reacting an epihalohydrin includes reacting epichlorohydrin.

This aspect, taken alone or combinable with any other aspect, can include the following features. Reacting a carboxylic acid includes reacting a carboxylic acid selected from acetic acid, propionic acid, and trifluoroacetic acid.

This aspect, taken alone or combinable with any other aspect, can include the following features. Reacting a carboxylic acid includes reacting acetic acid.

This aspect, taken alone or combinable with any other aspect, can include the following features. Reacting a carboxylic acid includes reacting propionic acid.

This aspect, taken alone or combinable with any other aspect, can include the following features. Reacting a carboxylic acid includes reacting trifluoroacetic acid.

This aspect, taken alone or combinable with any other aspect, can include the following features. Reacting a fatty acid modified with an amino alkyl group includes reacting N, N-dimetyl-erucyl-1,3,-propylenediamine.

The term "about" as used in this disclosure can allow for a degree of variability in a value or range, for example, within 10%, within 5%, or within 1% of a stated value or of a stated limit of a range.

The term "substantially" as used in this disclosure refers to a majority of, or mostly, as in at least about 50%, 60%, 70%, 80%, 90%, 95%, 96%, 97%, 98%, 99%, 99.5%, 99.9%, 99.99%, or at least about 99.999% or more.

The term "alkyl," employed alone or in combination with other terms, refers to a saturate hydrocarbon group that may be straight-chain or branched.

The terms "halo" or "halogen," used alone or in combination with other terms, refers to fluoro, chloro, bromo, and iodo.

The term "solvent" as used in this disclosure refers to a liquid that can dissolve a solid, another liquid, or a gas to form a solution. Non-limiting examples of solvents are silicones, organic compounds, water, alcohols, ionic liquids, and supercritical fluids.

As used in this disclosure, "weight percent" (wt %) can be considered a mass fraction or a mass ratio of a substance to the total mixture or composition. Weight percent can be a weight-to-weight ratio or mass-to-mass ratio, unless indicated otherwise.

A number of implementations of the disclosure have been described. Nevertheless, it will be understood that various modifications may be made without departing from the spirit and scope of the disclosure.

What is claimed is:

1. A process comprising reacting:
N,N-dimethyl-erucyl-1,3,-propylenediamine;
an epihalohydrin; and
a carboxylic acid selected from the group consisting of:

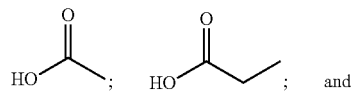

to afford a cationic surfactant with the structure of Formula II:

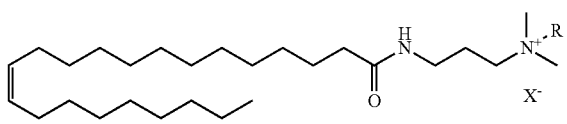

where R is selected from the group consisting of:

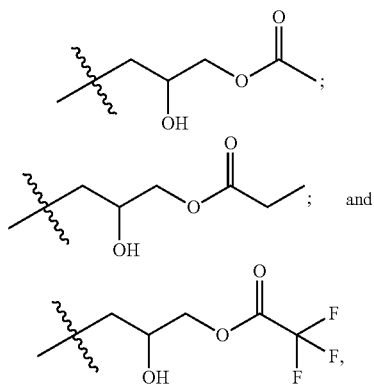

and where X is halide.

2. The process of claim 1, wherein reacting an epihalohydrin comprises reacting epichlorohydrin.

3. The process of claim 1, wherein reacting a carboxylic acid comprises reacting an acid having the structure

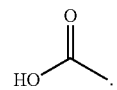

4. The process of claim 1, wherein reacting a carboxylic acid comprises reacting an acid having the structure

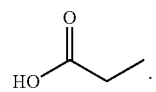

5. The process of claim 1, wherein reacting a carboxylic acid comprises reacting an acid having the structure

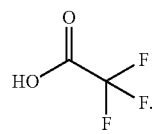

* * * * *

UNITED STATES PATENT AND TRADEMARK OFFICE
CERTIFICATE OF CORRECTION

PATENT NO. : 11,591,292 B2
APPLICATION NO. : 17/551945
DATED : February 28, 2023
INVENTOR(S) : Xuan Zhang, Ming Han and Jinxun Wang It is certified that error appears in the above-identified patent and that said Letters Patent is hereby corrected as shown below:

In the Claims

In Column 15, Line 49, Claim 1, replace "1,3,- propylenediamine;" with -- 1,3-propylenediamine; --.

Signed and Sealed this
Thirtieth Day of May, 2023

Katherine Kelly Vidal
*Director of the United States Patent and Trademark Office*